United States Patent [19]

Gross et al.

[11] Patent Number: 5,425,706

[45] Date of Patent: Jun. 20, 1995

[54] DISPENSING DEVICE PARTICULARLY USEFUL FOR DISPENSING NUTRITIONAL LIQUIDS

[75] Inventors: Jospeh Gross, Mazor; Shlomo Zucker, Yavne, both of Israel

[73] Assignee: S. I. Scientific Innovations Ltd., Petach Tikua, Israel

[21] Appl. No.: 479,888

[22] Filed: Feb. 14, 1990

Related U.S. Application Data

[63] Continuation-in-part of Ser. No. 393,739, Aug. 15, 1989.

[30] Foreign Application Priority Data

Feb. 24, 1989 [IL] Israel ......................... 89400
Jun. 30, 1989 [IL] Israel ......................... 90816

[51] Int. Cl.$^6$ ............................................. A61M 37/00
[52] U.S. Cl. ................................. 604/145; 604/143; 222/95
[58] Field of Search ............... 604/140, 141, 145, 151, 604/246, 143; 222/326, 386.5, 389, 61, 95

[56] References Cited

U.S. PATENT DOCUMENTS

| | | | |
|---|---|---|---|
| 1,681,320 | 8/1928 | Bergh et al. | 604/145 |
| 2,566,823 | 9/1951 | Cariffe | 604/145 |
| 3,023,750 | 3/1962 | Baron | 604/141 |
| 3,115,280 | 12/1963 | Battista | 222/95 |
| 3,308,818 | 3/1967 | Rutkowski | 604/403 X |
| 3,756,459 | 9/1973 | Bannister et al. | 604/141 X |
| 3,838,794 | 10/1974 | Cogley et al. | 604/141 X |
| 3,929,259 | 12/1975 | Fegley et al. | 222/61 |
| 4,335,835 | 6/1982 | Beigler et al. | 604/246 X |
| 4,613,327 | 9/1986 | Tegrarian et al. | 604/141 |
| 4,857,055 | 8/1989 | Wang | 604/141 X |

FOREIGN PATENT DOCUMENTS

| | | |
|---|---|---|
| 0209644 | 1/1987 | European Pat. Off. . |
| 2195461 | 8/1974 | France . |
| 8800665 | 1/1988 | WIPO . |

Primary Examiner—Gene Mancene
Assistant Examiner—L. Thomas
Attorney, Agent, or Firm—Benjamin J. Barish

[57] ABSTRACT

A dispensing device particularly useful for dispensing nutritional liquids includes an electrolytic cell having electrodes and an electrolyte capable of generating a gas upon the energization of the electrodes, which gas causes the dispensing of the liquid according to the rate of generation of the gas. The container for the liquid to be dispensed may be a disposable unit including the electrolytic cell, and a non-disposable electrical control circuit may be provided for controlling the rate of energization of the electrodes. The dispensing unit may also include an outer container adapted to receive a bag containing the liquid to be dispensed, the generated gas being applied between the outer container and the pliable bag.

29 Claims, 3 Drawing Sheets

DISPENSING DEVICE PARTICULARLY USEFUL FOR DISPENSING NUTRITIONAL LIQUIDS

RELATED APPLICATION

The present application is for a continuation-in-part of our Application Ser. No. 07/393,739, filed Aug. 15, 1989.

BACKGROUND OF THE INVENTION

The present invention relates to a dispensing device, and particularly to such a device for dispensing a nutritional liquid from a bottle, plastic bag, or other like container.

Our above Patent Application Ser. No. 07/393,739 discloses a dispensing device for dispensing a liquid at a predetermined rate, comprising a container for receiving a supply of liquid to be dispensed, and an electrolytic cell including electrodes adapted to be electrically energized, and an electrolyte capable of generating a gas upon the energization of the electrodes, to thereby force the liquid from the container in accordance with the rate of energization of the electrodes. That patent application discloses a number of preferred embodiments particularly useful for delivering medicaments to a patient at a predetermined rate.

An object of the present invention is to provide further embodiments of the invention of that patent application particularly useful for dispensing nutritional liquids, such as are now fed to patients by a peristaltic pump or by gravity.

More particularly, a main object of the present invention is to provide a dispensing device which is simple and hygienic to use especially for dispensing nutritional liquids.

Another object of the present invention is to provide a dispensing device of the electrolytic cell type which may be incorporated in or with the container containing the liquid to be dispensed, and which therefore may be disposable with the container, while the electrical control circuit for controlling the energization of the electrodes, and thereby the rate of dispensing of the liquid, is included in a separate, non-disposable unit for multitime use.

Another object of the invention is to provide an electrolytic cell type dispensing device which may be used with commercially-available bottles or plastic bags containing the liquid to be dispensed.

BRIEF SUMMARY OF THE INVENTION

According to the present invention, there is provided a dispensing device for dispensing a liquid, comprising a disposable container for the liquid to be dispensed; and having at one end a neck of reduced diameter and a disposable electrolytic cell removably attachable to the neck of the container. The electrolytic cell has electrodes adapted to be electrically energized, and an electrolyte capable of generating, upon the energization of the electrodes, a gas which forces liquid from the container in accordance with the rate of energization of the electrodes. An electrical control circuit included in a separate unit is removably attached to the electrolytic cell for controlling the rate of energization of the electrodes, and thereby the rate of dispensing of the liquid from the container.

A number of embodiments of the invention are described below for purposes of example.

In some described embodiments, the electrolytic cell is incorporated in a dispensing unit attached to the neck of the container and includes a feed tube extending into the bottle via its neck.

According to one such described embodiment, the electrolytic cell is of annular configuration to enclose the neck of the container when the dispensing unit is attached thereto, with the feed tube extending along the central axis of the annular electrolytic cell.

According to additional features in the described preferred embodiments, the dispensing device further includes a drip chamber having an upper end communicating with the outlet side of the feed tube externally of the container, and a lower end connectible to a delivery tube for delivering the dispensed liquid. The drip chamber preferably has a transparent outer wall to enable inspection of the feed rate, and preferably also includes a vent at its upper end containing a biological filter to vent the interior of the drip chamber to the atmosphere, and thereby to prevent the possibility of "dumping", i.e., a rapid discharge of the liquid to the patient by a siphonic action.

In other described embodiments, the disposable container includes a pliable bag open at one end; and an outer container enclosing the pliable bag. The electrolytic cell is attached to the dispensing device so as to pass the generated gas between the pliable bag and outer container to thereby force the liquid out of the pliable bag through its open end. The outer container may be a bottle which is more rigid than the pliable bag, or may be another pliable bag.

As will be more apparent from the description below, dispensing devices may be constructed according to the foregoing features such that the electrolytic cell is supplied with the container for the liquid to be dispensed as a disposable, one-time unit, and the electrical control circuit for controlling the rate of energization of the electrodes, and thereby the rate of dispensing the liquid, may be supplied as a separate, non-disposable control unit conveniently attachable to each disposable unit when its contents are to be dispensed. Such a dispensing device is therefore particularly useful for dispensing nutritional fluids to a patient in a simple and hygienic manner.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

The Embodiment of FIGS. 1–5

Figure 1:
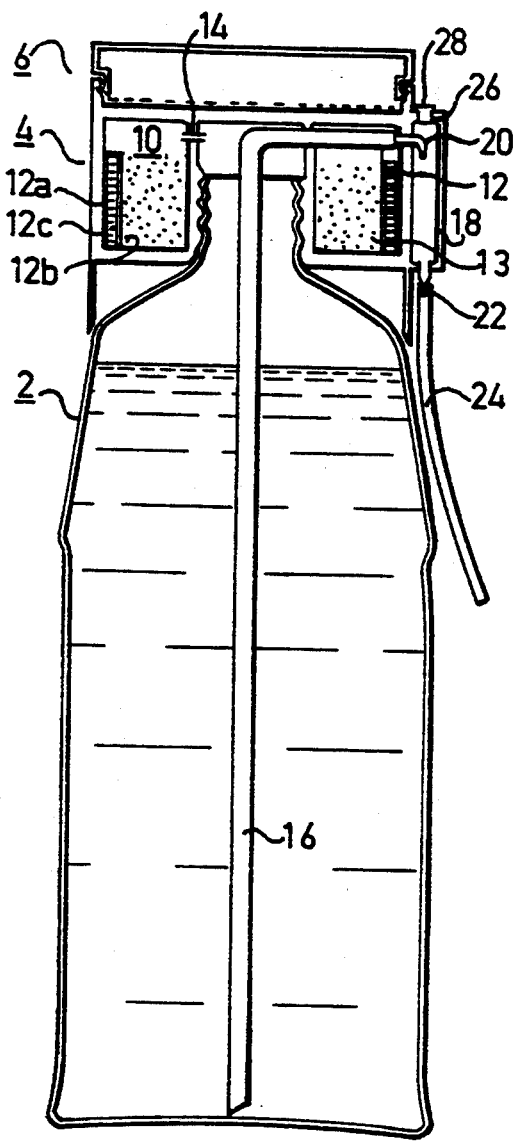
FIG. 1 illustrates one form of dispensing device constructed in accordance with the present invention.
Figure 2:
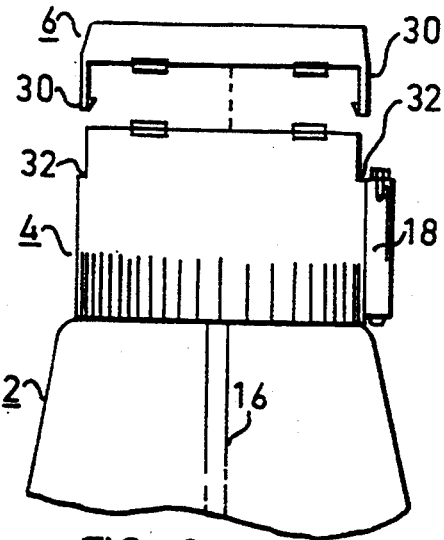
FIG. 2 is a fragmentary view illustrating the main components of the dispensing device of FIG. 1.
Figure 3:
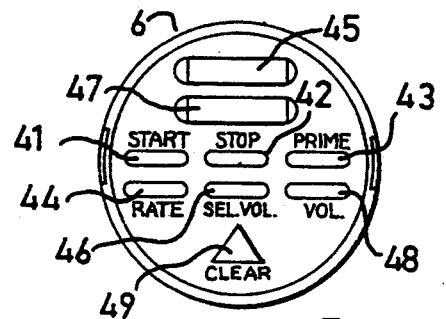
FIG. 3 is a plan view illustrating the control panel of the electrical control unit used with the dispensing device of FIGS. 1 and 2.

The dispensing device illustrated in FIGS. 1–4 is intended particularly for dispensing a liquid, especially a nutritional liquid, from a conventional bottle 2 in which the liquid is normally supplied. The dispensing device comprises a separate dispensing unit 4 including an electrolytic cell attachable to the neck of the bottle, and a control unit 6 which is attachable to the electrolytic cell unit 4. The dispensing unit 4 containing the electrolytic cell is intended to be supplied as a disposable unit for one-time use with the bottle 2 containing the liquid to be dispensed; whereas the control unit 6 is intended to be supplied as a non-disposable unit for multiple-time use by merely attaching it to the electrolytic cell unit 4 and then removing it from that unit when that unit has been depleted.

The dispensing unit 4 comprises an annular chamber 10 containing electrodes, generally designated 12, adapted to be electrically energized, and an electrolyte 13 capable of generating a gas upon the energization of the electrodes, which gas is fed via a passageway 14 into the interior of the bottle 2. Unit 4 further includes a feed tube 16 extending through the central axis of the annular chamber 10 so as to pass through the bottle neck into the bottle with its lower end slightly spaced from the bottom of the bottle.

A drip chamber 18 is fixed to one side of the dispensing unit 4 externally of the bottle 2. The outlet end 20 of feed tube 16 is received in the upper end of drip chamber 18, and the lower end of the drip chamber includes a nipple 22 for receiving a delivery tube 24 for delivering the dispensed liquid to the patient.

Drip chamber 18 is of tubular construction. It includes a transparent outer wall to permit viewing the interior of that chamber, and thereby the rate of feed of the liquid to the patient. The upper end of drip chamber 18 is further formed with a vent 26 venting the interior of the chamber to the atmosphere. Vent 26 is covered by a biological filter 28 to prevent contamination of the liquid passing through the drip chamber to the patient. The provision of vent 26 prevents the possibility of "dumping" i.e., of a very rapid discharge of the liquid from the bottle to the patient by siphonic action.

The electrolyte 13 included within compartment 10 may be any material, preferably a liquid, which generates a gas when its electrodes 12 are energized. Preferably, the electrolyte is distilled water including a small quantity of a salt. Particularly good results have been obtained by using distilled water with about 2% sodium bicarbonate. Such an electrolyte generates both hydrogen and oxygen when its electrodes 12 are energized.

The electrodes 12 are of annular configuration as shown in FIG. 1. Particularly good results have been obtained when the electrodes include two metal screens or meshes 12a, 12b, spaced apart by a screen or mesh 12c of insulating material. As one example, the electrodes 12a, 12 may be an open screen of stainless steel wires of 0.2 mm diameter; and the insulating spacer 12c may be a plastic screen of nylon threads of 0.4 mm diameter.

The control unit 6 is attachable to the dispensing unit 4 by a quick-attaching arrangement, such as by the provision of hooks 30 depending below unit 6 receivable within grooves 32 formed in the upper face of the dispensing unit 4. When unit 6 is thus attached to unit 4, electrical connections are made between the two units via electrically conductive strips 34 on unit 6 in contact with conductive strips 36 on unit 4.

Figure 4:
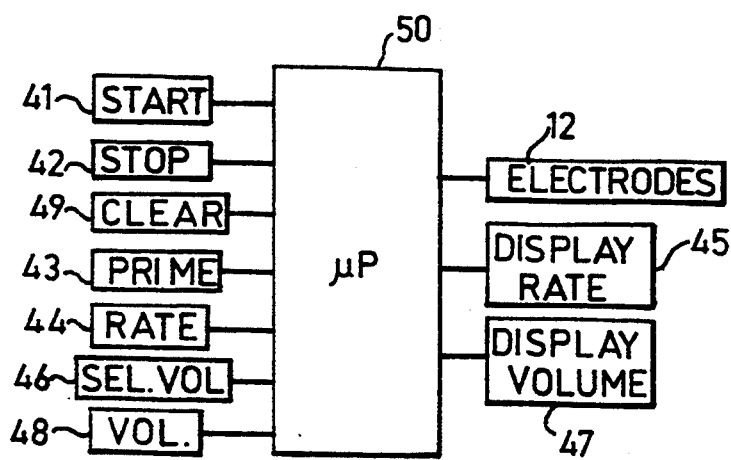
FIG. 4 is a block diagram of the electrical circuit in the control unit.

The control unit 6 may include its own batteries, or may be connected to the supply mains, FIG. 4 illustrates the various control buttons and displays.

Thus, control unit 6 includes a Start button 41 and a Stop button 42 for starting and stopping the dispensing of the liquid. It further includes a Prime button 43 for initially generating gas at a rapid rate in order to prime the dispensing unit, i.e., to completely fill its feed tube 16 and delivery tube 24 with the liquid, before the delivery tube is applied to the patient to receive the dispensed liquid.

Control unit 6 further includes a Rate button 44 which is used to preset the rate of energization of the electrodes 12, and thereby the rate of feeding of the liquid to the patient after the device has been primed. To select the rate, button 44 is depressed, which causes the rates to "roll" through the rate display 45 until the selected rate appears, at which time the button is released. The preselected rate is thus viewable in the rate display 45.

Control unit 6 further includes a Select-Volume button 46 which is used to select the total volume of liquid to be dispensed. This volume is also selected by a "rolling" action, i.e., by depressing button 46 until the selected volume appears in the Volume display 47, whereupon the button is released, so that the selected volume now appears in display 47.

Control unit 6 further includes a Volume button 48, which is depressed in order to view the total volume already dispensed. This is also displayed in Volume display 47 when button 48 is depressed; at all other times, Volume display 47 shows the selected volume as selected by depressing button 46.

Finally, control unit 6 further includes a Clear button 49 to clear all the data previously inputted.

The control itself is effected by a microprocessor, generally designated 50, as illustrated in FIG. 4. Thus, the microprocessor 50 receives, as inputs, the information from the buttons 41–44, 46, 48 and 49, and controls the two displays 45 and 47, as described above. Microprocessor 50 also controls the energization of the electrodes 12 according to the selected rate of dispensing the liquid. It also controls the total volume to be dispensed as selected by Select-Volume button 46 and displayed in display 47, and continuously computes the volume actually dispensed and displayed in display 47 upon depression of Volume button 48.

Figure 5:
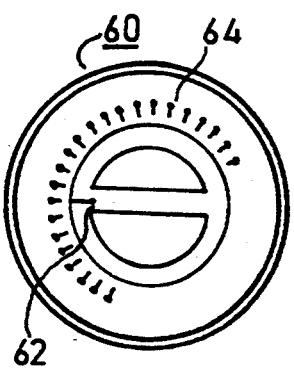
FIG. 5 is a plan view of the control panel of another type of control unit which may be used.

FIG. 5 illustrates a control panel of a simpler control unit 60 which may be used instead of unit 6. The simpler control unit 60 includes only one control member 62 cooperable with a scale 64 to permit the user to select the rate of energization of the electrodes, and thereby the rate of dispensing of the liquid. Such a simple control circuit obviates the need for a microprocessor, and enables a simple current-variable circuit (e.g., potentiameter), or voltage-variable circuit (e.g., voltage divider), to be used for controlling the rate of energization of the electrodes.

It will thus be seen that the dispensing device illustrated in FIGS. 1–5 may include a disposable dispensing unit incorporated with or attached to the bottle so as to be disposable with the bottle, and a non-disposable control unit 6 for multiple-time use. Such a construction provides an arrangement which is both simple and hygienic to use, and thereby makes it particularly useful for dispensing nutritional liquids, infusion liquids, and the like.

The Embodiments of FIGS. 6–9

FIGS. 6–9 illustrate further embodiments that are particularly useful where it is not desired that the gas generated by the electrolytic cell come into direct contact with the liquid to be dispensed. In such cases, the liquid to be dispensed is supplied in a pliable plastic bag, and the gas generated by the electrolytic cell is applied to the space between the outer face of the plastic bag and the inner face of another container, e.g., a bottle or another plastic bag.

Figure 6:
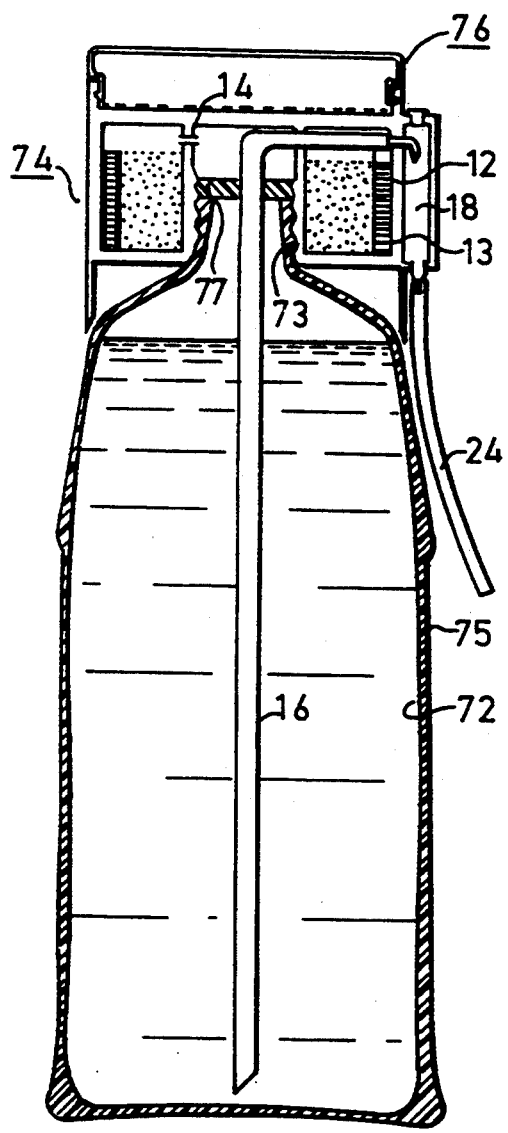
FIGS. 6 and 7 illustrate other forms of dispensing devices constructed in accordance with the present invention for use in dispensing liquids supplied in pliable plastic bags.

Thus, FIG. 6 illustrates a construction wherein the liquid to be dispensed is supplied in a container which includes a plastic bag 72 and an outer relatively rigid bottle 75 (i.e., more rigid than plastic bag 72), having a neck 73 at its upper end. The dispensing unit 74 is attached to neck 73.

Dispensing unit 74 is constructed of basically the same structure as described above, particularly with respect to FIG. 1; to facilitate understanding, the same reference numerals have therefore been applied. The dispensing unit 74, however, further includes a passageway 77 through the rigid neck 73 of the plastic bag 72, which passageway directs the gas generated in the electrolytic cell, and exiting through opening 14, to the space between the outer surface of the plastic bag 72 and the inner surface of the rigid bottle 75. Accordingly, the pressure in this space will increase according to the rate of the generation of the gas so as to compress the plastic bag 72, and thereby to dispense the liquid therefrom via feed tube 16, drip chamber 18, and delivery tube 24, according to the rate of energization of the electrodes 12 within the electrolyte 13.

In the embodiment of FIG. 6, the plastic bag 72, bottle 75, and dispensing unit 74 may all be disposable after one-time use. The control unit 76, however, is preferably constructed as a non-disposable unit for quick attachment to the dispensing unit 74 for multiple-time use.

Figure 7:
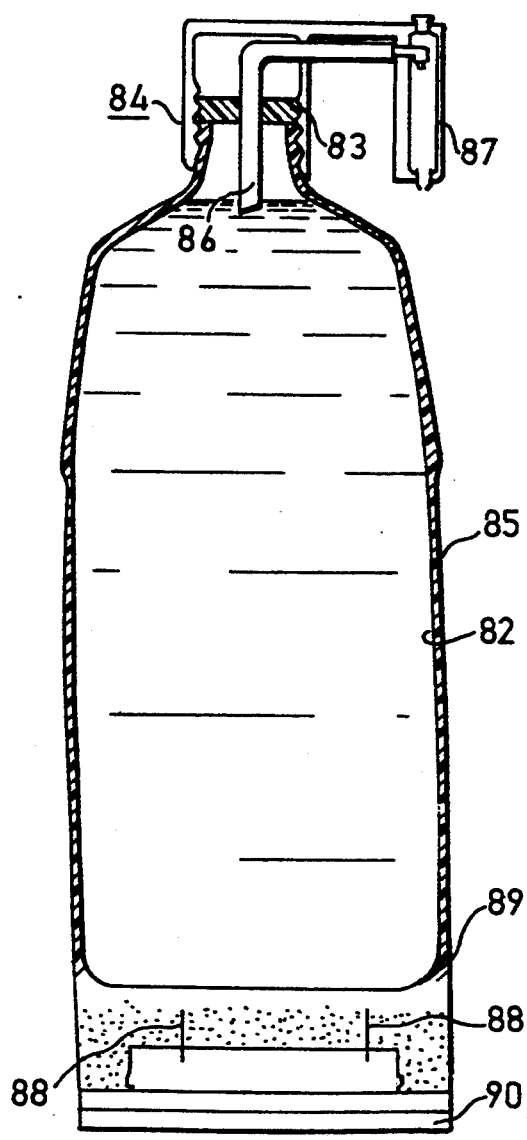

FIG. 7 illustrates another construction for use with a plastic bag container 82 for the liquid to be dispensed. This construction also includes a dispensing unit 84 and an outer, relatively rigid bottle 85, both attachable to the neck 83 of the plastic bag 82. In this case, dispensing unit 84 includes only the feed tube 86 and drip chamber 87, corresponding to feed tube 16 and drip chamber 18 in FIG. 1. The electrolytic cell is disposed in the bottom of the bottle 85, which bottom includes the electrodes 88 and electrolyte 89. The arrangement is such that energization of the electrodes causes the electrolyte 89 to generate a gas from the bottom of the bottle 85 into the space between the plastic bag 82 and the bottle, to compress the bag and thereby to dispense liquid via the feed tube 86 and drip chamber 87 according to the rate of energization of the electrodes.

All the foregoing elements in FIG. 7 may be constructed as a disposable unit for one-time use. The control of the energization of the electrodes 88, however, is effected by a control unit 90, of a construction as described above with reference to FIGS. 4 or 5, which is non-disposable and quickly attachable to the disposable unit for multiple use.

Figure 8:
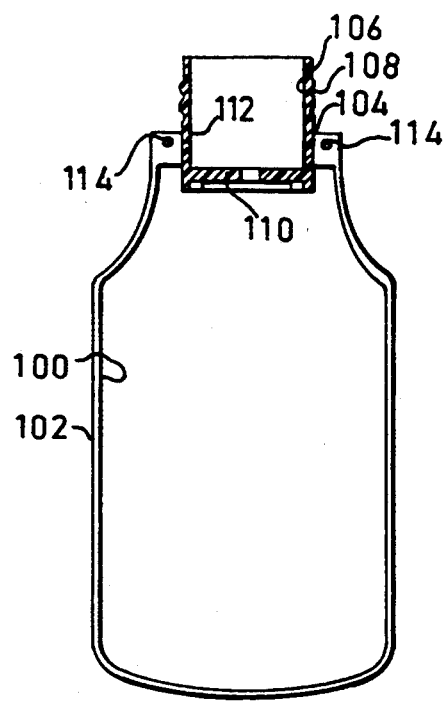
FIG. 8 illustrates a part of a further form of dispensing unit constructed in accordance with the present invention for dispensing liquids supplied from plastic bags.

FIG. 8 illustrates a construction wherein the outer container, enclosing the plastic bag containing the liquid to be dispensed, is also in the form of a plastic bag. Thus, the dispensing device illustrated in FIG. 8 comprises an inner plastic bag 100, for containing the liquid to be dispensed, enclosed within an outer plastic bag 102. Both plastic bags are secured, at their upper open ends, to a rigid unit 104 formed with a rigid neck 106 having external threads 108 adapted to receive a dispensing unit, such as unit 74 illustrated in FIG. 6. When such a dispensing unit is applied, the feed tube 16 passes through an opening 110 in unit 104 into the interior of bag 100; and the gas generated by the electrolytic cell included in such unit passes through an opening 112 into the space between the two plastic bags 110, 102. The gas thereby compresses bag 100 in accordance with the rate of gas generated, to dispense the liquid from bag 100 via the feed tube, as described above. Unit 104 is further formed with a pair of openings 114 to permit the dispensing unit to be supported in suspension.

All the elements included in the construction illustrated in FIG. 8 would also preferably be provided for one-time use, together with the electrolytic cell and feed tube, whereas the electrical control unit, e.g., 76 in FIG. 6, would preferably be supplied for multiple-time use as also described above. For the sake of simplicity, the disposable dispensing unit including the electrolytic cell and feed tube, and the control unit including the circuitry for controlling the energization of the electrodes in the electrolytic cell, are not illustrated in FIG. 8, but it will be appreciated that they may be of the same construction as dispensing unit 74 and control unit 76 in FIG. 6.

Figure 9:
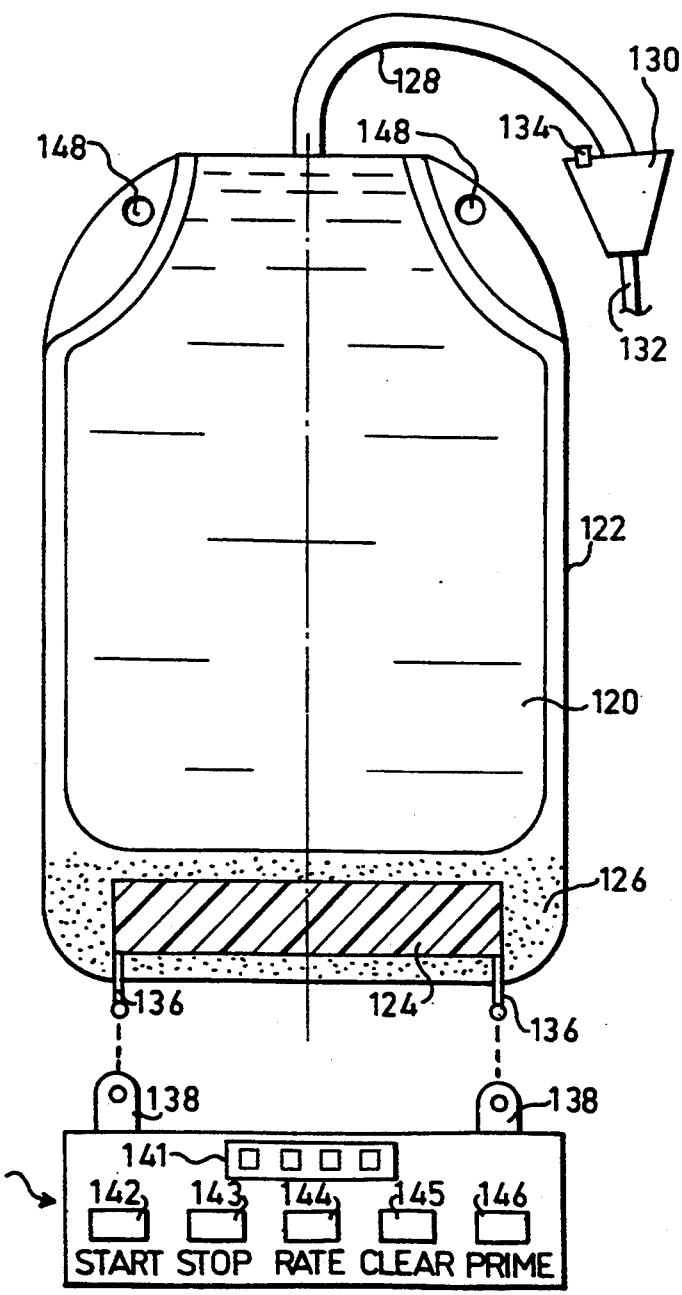
FIG. 9 illustrates a further dispensing device constructed in accordance with the present invention for supplying liquids from plastic bags.

FIG. 9 illustrates a still further construction wherein the disposable unit also includes a plastic bag 120 containing the liquid to be dispensed, and an outer bag 122 enclosing bag 120. In this construction, the electrolytic cell including the electrodes 124 and electrolyte 126 are provided in the bottom of the outer bag 122 such that the gas generated by the energization of the electrodes passes into the space between the two bags, and thereby compresses the inner bag 120 to force out the liquid from its upper, open end according to the rate of energization of the electrodes. The upper, open end of bag 120 is provided with a feed tube 128 connected to a drip chamber 130, which is in turn connected to a delivery tube 132 for delivering the dispensed liquid to the patient. As described above, drip chamber 130 is also of transparent material to permit viewing its interior, and thereby the rate of dispensing of the liquid to the patient, and is further provided with a vent 134 occupied by a biological filter to prevent "dumping" by siphonic action.

The outer bag 122 is provided with a pair of terminals 136 for connection to the terminals 138 of a control unit 140 controlling the rate of energization of the electrodes 124, and thereby the rate of dispensing of the liquid. Control unit 140 may have the same controls as described above with respect to FIGS. 4 or 5. However, for purposes of example, the control unit 140 illustrated in FIG. 9 is of intermediate complexity compared to those of control units 4 and 5. It includes only a single display 141, displaying the actual rate of delivery of the dispensed liquid, a Start button 142, a Stop button 143, a Rate button 144, a Clear button 145, and a Prime button 146, functioning in the same manner as described above with respect to FIG. 4.

The construction illustrated in FIG. 9 further includes a pair of openings 148, at the upper end of the outer plastic bag 122, to permit supporting the unit in suspension.

It will be appreciated that the embodiments of the invention described below are set forth merely for purposes of example, and that many variations and modifications may be made. For example, if the liquid to be dispensed is located at a lower elevation than the subject receiving it, the vent 26 in the drip chamber, and also the drip chamber itself, may not be needed. The described electrodes and electrolyte are also set forth merely for purposes of example and many other materials may be used generating other types of gasses, according to the particular application. Because of the advantages of simplicity and hygiene in using the illustrated constructions, these constructions are described particularly for use for feeding nutritional liquids to patients, but it will be appreciated that the devices can be used in many other medical applications (e.g., the infusion of liquids), as well as in many non-medical applications. Many other variations, modifications and applications of the invention may be made.

What is claimed is:

1. A dispensing device for dispensing a liquid, comprising:
   a disposable container for the liquid to be dispensed, said container having at one end a rigid neck of reduced diameter;
   a disposable electrolytic cell removably attachable to said neck of the container, said electrolytic cell having electrodes adapted to be electrically energized, and an electrolyte capable of generating, upon the energization of the electrodes, a gas which passes through said neck into the container and forces liquid out from the container in accordance with the rate of energization of the electrodes;
   and an electrical control circuit included in a separate unit removably attached to said electrolytic cell for controlling the rate of energization of the electrodes, and thereby the rate of dispensing of the liquid from the container.

2. The dispensing device according to claim 1, wherein said electrolytic cell is incorporated in a dispensing unit attached to the bottle neck and includes a feed tube extending through the container neck.

3. The dispensing device according to claim 2, wherein said electrolytic cell is included with said feed tube in said dispensing unit attached to the bottle neck, said electrolytic cell being of annular configuration to enclose the bottle neck when the dispensing unit is attached thereto, with said feed tube extending along the central axis of the annular electrolytic cell.

4. The dispensing device according to claim 3, wherein said electrodes in the annular electrolytic cell are also of annular configuration.

5. The dispensing device according to claim 2, further including a drip chamber having an upper end communicating with the outlet side of said feed tube externally of the container, and a lower end connectible to a delivery tube for delivering the dispensed liquid.

6. The dispensing device according to claim 1, wherein said disposable container includes a pliable bag open at one end; and an outer container enclosing said pliable bag; said electrolytic cell being attached to said neck so as to pass the generated gas between the pliable bag and outer container to thereby force the liquid out of said pliable bag through its open end.

7. The dispensing device according to claim 6, wherein said electrolytic cell includes a feed tube extending through the upper open end of the pliable bag, and a passageway for directing the generated gas between the pliable bag and the outer container.

8. The dispensing device according to claim 6, wherein said electrolytic cell is located within the outer chamber at the lower end thereof, such that the generated gas is passed between the pliable bag and outer container.

9. The dispensing device according to claim 6, wherein said outer container is a bottle having substantially more rigidity than said pliable bag.

10. The dispensing device according to claim 6, wherein said outer container is another pliable bag.

11. A dispensing device for dispensing a liquid at a predetermined rate, comprising:
    a container for containing the liquid to be dispensed, and including a rigid neck of reduced diameter at its upper open end;
    a dispensing unit attachable to the neck of the container and including a feed tube to pass through the container neck into the container for immersion in the liquid contents of the container, when the dispensing unit is attached to the container neck;
    said dispensing unit including an electrolytic cell having electrodes adapted to be electrically energized, and an electrolyte capable of generating, upon the energization of the electrodes, a gas which passes through said neck into the container and forces liquid from the container through said feed tube in accordance with the rate of energization of said electrodes;
    and an electrical control circuit for controlling the rate of energization of the electrodes and thereby the rate of generation of the gas.

12. The dispensing device according to claim 11, wherein said electrolytic cell is of annular configuration to enclose the neck of the container when the dispensing unit is attached thereto, with said feed tube extending along the central axis of said annular electrolytic cell.

13. The dispensing device according to claim 12, wherein said electrodes in the annular electrolytic cell are also of annular configuration.

14. The dispensing device according to claim 11, wherein said dispensing unit further includes a drip chamber having an upper end communicating with said feed tube externally of the container, and a lower end connectible to a delivery tube for delivering the dispensed liquid.

15. The dispensing device according to claim 14, wherein said drip chamber has a transparent outer wall.

16. The dispensing device according to claim 14, wherein said drip chamber includes a vent at its upper end to vent the interior thereof to the atmosphere.

17. The dispensing device according to claim 16, wherein said vent includes a biological filter to filter the air entering the drip chamber via said vent.

18. The dispensing device according to claim 11, wherein said electrical control circuit is in a separate unit attachable to said dispensing unit for controlling the rate of energization of said electrodes, and thereby the rate of dispensing of said liquid.

19. The dispensing device according to claim 11, wherein said container includes a pliable bag and a bottle dimensioned to enclose said bag.

20. The dispensing device according to claim 19, wherein said electrolytic cell is located at the upper end of the bottle and includes a passageway passing the generated gas between the inner face of the bottle and the outer face of the bag.

21. The dispensing device according to claim 19, wherein said electrolytic cell is located at the bottom end of the bottle, and passes the generated gas between the inner face of the bottle and the outer face of the bag.

22. The dispensing device according to claim 21, wherein said electrolytic cell is in a separate unit attachable to the bottom end of the bottle.

23. The dispensing device according to claim 11, wherein said electrical control circuit includes a Prime control member for initially generating the gas at a rapid rate in order to prime the dispensing unit; and a Rate control member for preselecting the rate of generation of said gas and thereby the rate of dispensing of the liquid after priming the dispensing unit.

24. The dispensing device according to claim 11, wherein said electrodes include a pair of metal screens separated by a plastic screen.

25. The dispensing device according to claim 11, wherein said electrodes are of annular configuration.

26. A dispensing device attachable to the neck of a container containing a liquid to be dispensed via an open end thereof; said dispensing device comprising:

a feed tube to pass through the open end of the container for immersion in the liquid contents of the container when the dispensing device is attached thereto;

an electrolytic cell including electrodes adapted to be electrically energized, and an electrolyte capable of generating a gas upon the energization of the electrodes, which gas is applied to the container to force liquid therefrom via said feed tube in accordance with the rate of energization of the electrodes;

and an electrical control circuit for controlling the rate of energization of the electrodes, and thereby the rate of dispensing of the liquid.

27. The dispensing device according to claim 26, wherein said electrolytic cell is of annular configuration to enclose the neck of the container when the dispensing device is attached thereto, said feed tube extending along the central axis of the annular electrolytic cell for passage through the open end of the container when the device is attached thereto.

28. The dispensing device according to claim 26, further including a drip chamber having an upper end communicating with the outlet side of said feed tube externally of the container, and a lower end connectible to a delivery tube for delivering the dispensed liquid.

29. The dispensing device according to claim 26, wherein said electrical control circuit is in a separate unit attachable to said electrolytic cell.

* * * * *